United States Patent [19]

Griffith et al.

[11] 4,024,256

[45] May 17, 1977

[54] METHOD AND COMPOSITION FOR TREATING URINARY TRACT INFECTIONS

[76] Inventors: Donald P. Griffith, 4425 Hazelton; Daniel M. Musher, 4903 Heatherglen, both of Houston, Tex. 77035

[22] Filed: Sept. 18, 1975

[21] Appl. No.: 614,684

Related U.S. Application Data

[63] Continuation-in-part of Ser. No. 441,245, Feb. 11, 1974, abandoned.

[52] U.S. Cl. .............................. 424/249; 424/320
[51] Int. Cl.² ........................................ A61K 31/53
[58] Field of Search .................... 424/81, 249, 320

[56] References Cited

OTHER PUBLICATIONS

Chemical Abstracts 63: 16994f (1965).
The Merck Index, 8th Ed., Merck & Co., Inc., 1968, p. 673.
Musher et al., Antimicrobial Agents and Chemotherapy, Feb. 1974, vol. 5, No. 2, pp. 101–105.

*Primary Examiner*—Jerome D. Goldberg
*Attorney, Agent, or Firm*—Arnold, White & Durkee

[57] ABSTRACT

A method for the treatment of urinary tract infections and a composition for use in such method, such method comprising administering to a patient suffering from a urinary tract infection an effective anti-bacterial dosage of a composition comprising in combination:

a. a source of methenamine, e.g. methenamine; and
    b. a source of hydroxamate groups, e.g., acetohydroxamic acid.

The source of hydroxamate groups is administered in the amount effective to potentiate the anti-bacterial effect of the source of methenamine. The method is specifically applied to the treatment of urinary infections caused by urease producing bacteria, especially bacteria of the species *proteus*.

In addition, where colonization of the bacteria can be tolerated and where it is only necessary to eliminate the pathogenicity of the urease producing bacteria induced infection, effective treatment can be achieved by administration of only the source of hydroxamate groups, preferably acetohydroxamic acid. Also, by maintaining the urine at an acid pH in the presence of urease producing bacteria by administering a source of hydroxamate groups, struvite and apatite urinary stones normally associated with urease producing bacteria can be dissolved.

6 Claims, 17 Drawing Figures

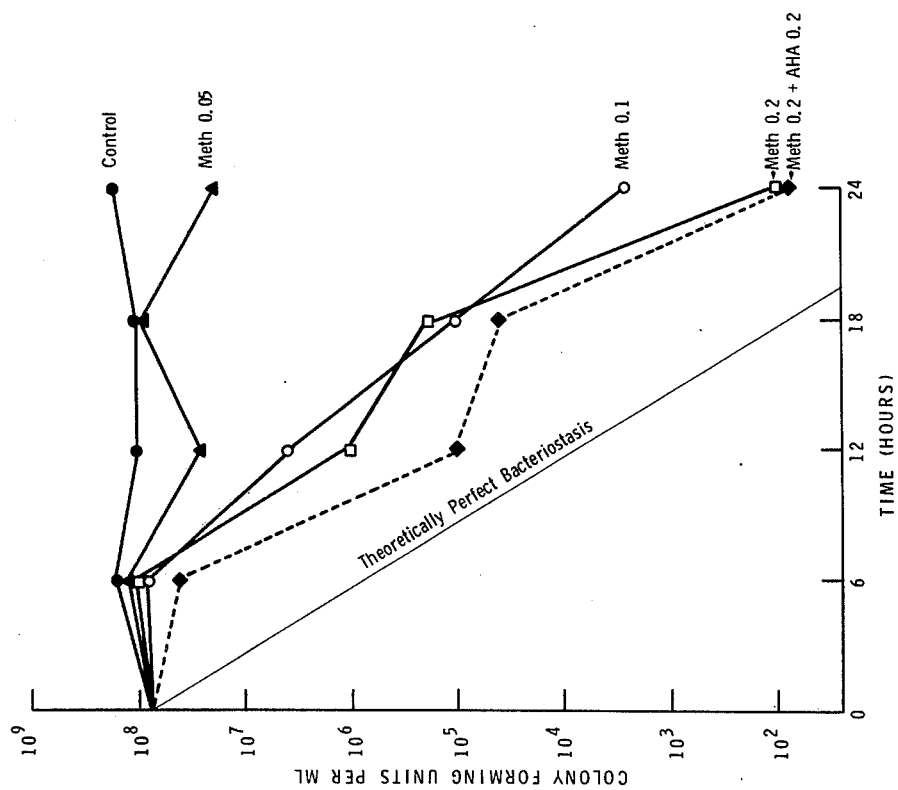
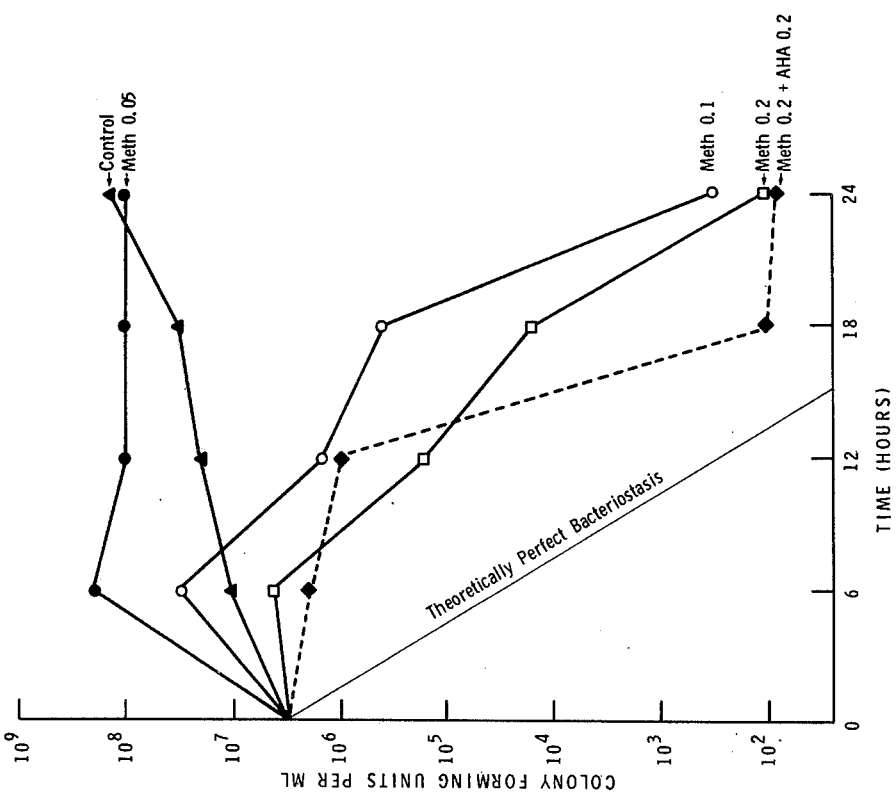

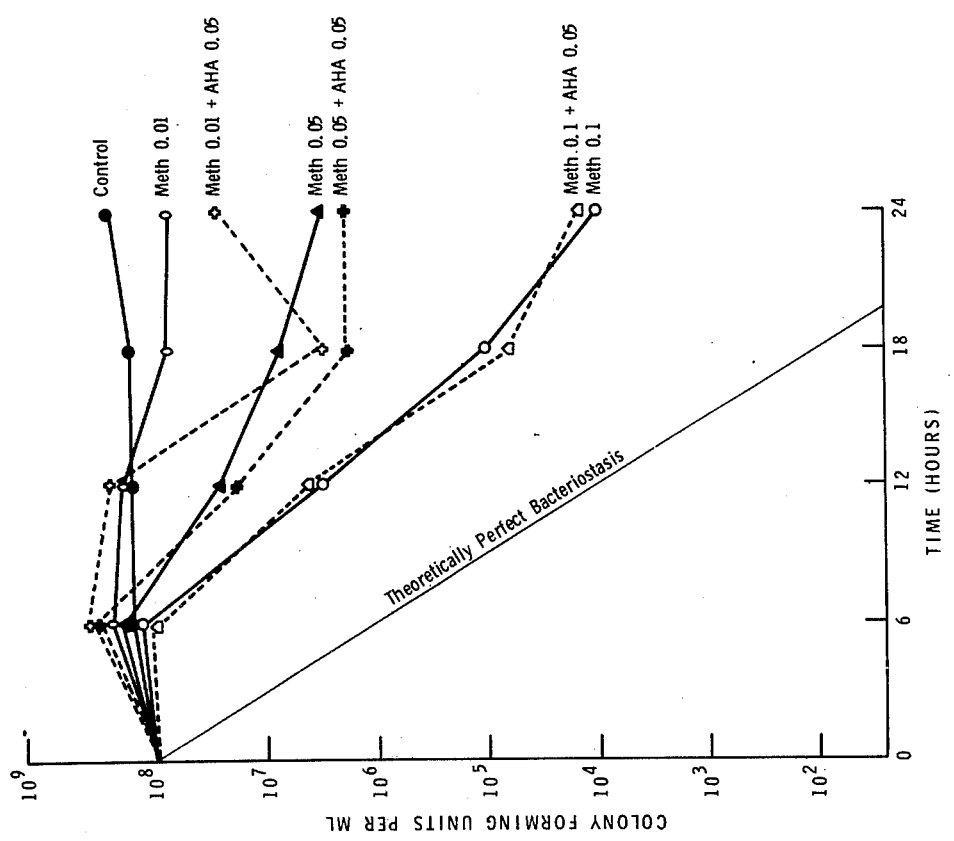
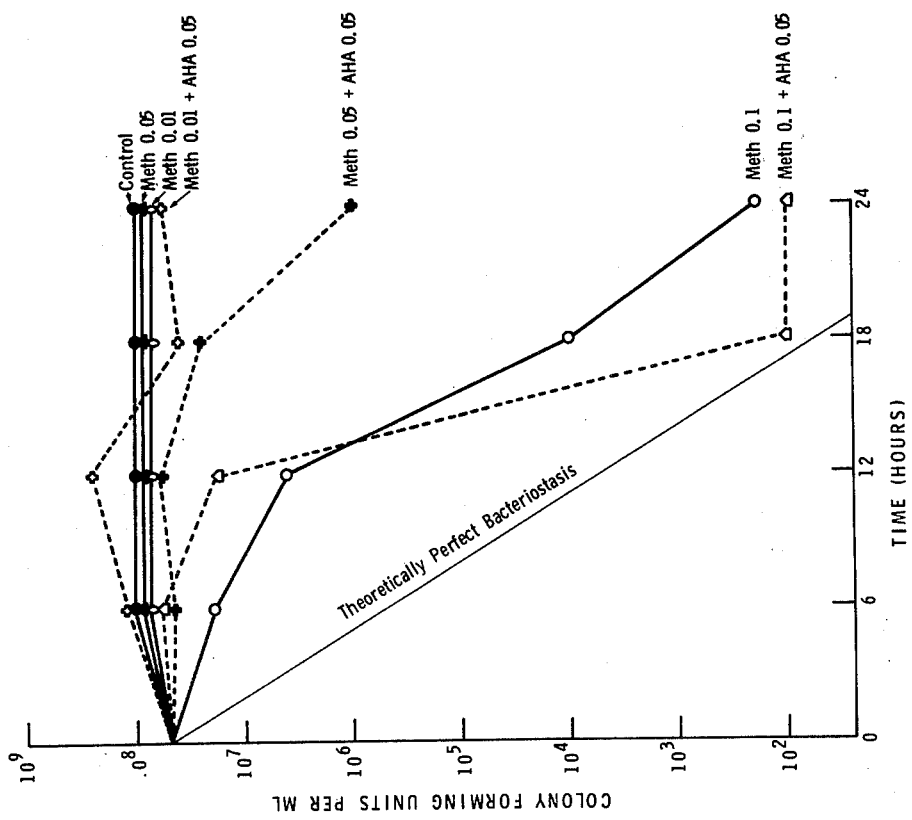

METHOD AND COMPOSITION FOR TREATING URINARY TRACT INFECTIONS

RELATED APPLICATION

This application is a continuation-in-part of application Ser. No. 441,245, filed Feb. 11, 1974, now abandoned.

BACKGROUND OF THE INVENTION

1. Field of Invention

This invention relates to a method for treating urinary tract infections and a composition for use in such method; and more specifically the present invention relates to such method and composition for the treatment of urinary tract infections, specifically urinary tract infections caused by bacteria that produce urease, especially those of the species Proteus, wherein the anti-bacterial effect of methenamine is potentiated or synergized by administering a source of methenamine in combination with a source of hydroxamate groups. In addition, this invention relates to a method of eliminating the pathogenicity of urease producing bacteria by administering to a patient suffering from an infection caused by urease producing bacteria a source of hydroxamate groups. Furthermore, the present invention provides a method of dissolving struvite and apatite urinary stones generally associated with urease producing bacteria by administering a source of hydroxamate groups which provides urine of physiological pH, which due to under-saturation with respect to struvite and apatite crystals can effectively dissolve the associated stones.

2. Description of the Prior Art

The increasing awareness of the importance of urinary tract infections has brought about the realization that adequate drug therapy is required for the treatment of the infection. With this awareness for the need for adequate drug therapy, a corresponding awareness has developed that such adequate drug therapy is difficult to provide.

For example, patients with urinary tract infections often have an associated condition of stasis, stone or obstruction in the urinary tract and the chronicity or recurrence of the urinary tract infections renders unlikely successful treatment. Where such conditions exist and where the infection reoccurs, antibiotics often lose their effect due to the rapid development or acquisition of resistant mutant organisms. Still further, when a patient has a urinary stone, while the infection might be satisfactorily treated initially with a conventional antiobiotic, the stone contains viable bacteria which serve as a source for reinfection. Accordingly, while conventional antibiotics may provide short time relief from urinary tract infections complete cure freuently cannot be achieved through the administration of the conventional antibiotic agent. However, with synthetic anti-bacterial agents, the development of resistance is much less common.

Based upon the effectiveness of synthetic anti-bacterial agents in the treatment of urinary tract infections, methenamine has had a traditional role for some time in this treatment. Methenamine was first synthesized in 1860 and the use of methenamine in the treatment of cystitis was reported as early at 1894. The methenamine exerts its anti-bacterial effect in an acid medium by releasing formaldehyde in a concentration which is bacteriostatic or bactericidal to virtually all known bacteria.

Methenamine, hexamethenamine tetramine, a tertiary amine, has properties of a monoacidic base in its salt formation. As a result different forms of methenamine have been developed and made available as a salt of methenamine and a pharmacologically aceptable organic acid. These forms were developed since they presumably acidify the urine, thereby enhancing the effect of methenamine, which can effectively release the active formaldehyde only in an acid urine. In addition, some anti-bacterial action for the organic acids themselves has been described; however, these agents have proven to be ineffective in acidifying urine in the presence of infection of the urinary tract associated with urea-spliting pathogens. In this respect nearly all species of Proteus and a number of strains of Pseudomonas, Klebsiella, E. Coli and Staphlococcus produce urease, an enzyme which splits the urea according to the following reaction:

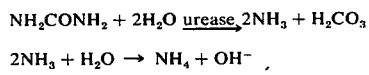

$$2NH_3 + H_2O \rightarrow NH_4 + OH^-,$$

The hyperammonuria and alkalinity which result through the foregoing reaction appear to be necessary for the precipitation of struvite ($MgNH_4PO_4 \cdot 6H_2O$), the predominant component of infected urinary calculi. This alkalinity eliminates the anti-bacterial activity of methenamine and compounds based on methenamine, thereby making these materials ineffective anti-bacterial agents for treatment of infection due to urease producing uropathogens when used in typical anti-bacterial dosages.

Due to the foregoing, where a patient is suffering from a urinary tract infection associated with certain urease producing bacteria, especially species of Proteus, the commonly employed anti-bacterial agent methanamine and compounds based on methenamine are ineffective in the treatment of the infection due to the hyperammonuria and alkalinity which result from the urease producing bacteria. Such alkalinity prevents the conversion of methanamine to its active anti-bacterial from formaldehyde. Based upon the foregoing, the art has long sought a method of treating urinary tract infections and a composition for use in such method which can eliminate the foregoing problem by maintaining physiologic acidity of urine and thereby provide the necessary environment for effective methenamine conversion to formaldehyde, even in the presence of urease producing bacteria.

SUMMARY OF THE INVENTION

It has now been discovered in accordance with the present invention that the foregoing disadvantages and drawbacks of previously proposed procedures for treatment of urinary tract infections can be eliminated through the provision of the method and composition of the present invention whereby a patient suffering from urinary tract infection, especially an infection caused by bacteria of the species Proteus is administered an effective anti-bacterial dosage of a composition which comprises in combination (a) a source of methanamine, e.g., methenamine and (b) a source of hydroxamate groups, e.g., acetohydroxamic acid, the source of hydroxamate groups being administered in an amount effective to potentiate or synergize the antibacterial effect of the source of methenamine by preventing the alkalinization normally induced by urease producing bacteria.

In connection with the above it has been discovered in accordance with the present invention that the administration of a source of hydroxamate groups, preferably acetohydroxamic acid in combination with a source of methenamine allows the methanamine to act as an effective anti-bacterial agent in the treatment of a urinary tract infection in that the source of hydroxamate groups as a urease inhibitor eliminates the alkalinization associated with the bacterial urease invariably produced by Proteus and some other species of bacteria, which alkalinization has heretofore eliminated the effectiveness of the methenamine.

Potentiation of the anti-bacterial effect of a source of methenamine by a source of hydroxamate groups is observed in accordance with the present invention at a urinary concentration of methenamine of from about 0.05 to about 1.0 mg/ml and a urinary concentration of hydroxamate groups of from about 0.05 to about 2.0 mg/ml.

In addition, it has now been discovered in accordance with the present invention that the urinary pathogenicity of urease producing bacteria induced infection can be eliminated by administering to a patient suffering from such infection an effective amount of a source of hydroxamate groups, e.g., acetohydroxamic acid. This result which is achieved in accordance with the present invention is predicated upon the discovery that the pathogenicity of the infection is associated with the urease production, the inhibiting of which, by the administration of a urease inhibitor, can effectively eliminate the pathogenicity of the bacteria, while not affecting the colonization of the bacteria. Again however, the pathogenicity and colonization can be eliminated by the conjoint administration of both the source of methenamine and the source of hydroxamate groups.

In has been further discovered in accordance with the present invention that urinary stones, e.g., struvite and apatite stones generally associated with urease producing bacteria can be effectively dissolved by administering a source of hydroxamate groups, e.g., acetohydroxamic acid, which source of hydroxamate groups has the effect of bringing about a physiological pH in the urine, with under-saturation with respect to struvite and apatite crystals.

When a source of hydroxamate groups is administered alone in accordance with the present invention a therapeutic urinary concentration of hydroxamate groups of from about 0.05 to about 2.0 mg/ml has been found to be very effective.

BRIEF DESCRIPTION OF THE DRAWINGS

FIGS. 4–15 are plots of time in hours vs. colony forming units per milliliter for Experiments A-L, respectively of Example 3, illustrating the synergistic effect of acetohydroxamic acid on methenamine in a static-dynamic study with *Proteus mirabilis, Proteus rettgeri* and *Proteus morgani;*

DESCRIPTION OF PREFERRED EMBODIMENTS

Figure 2:
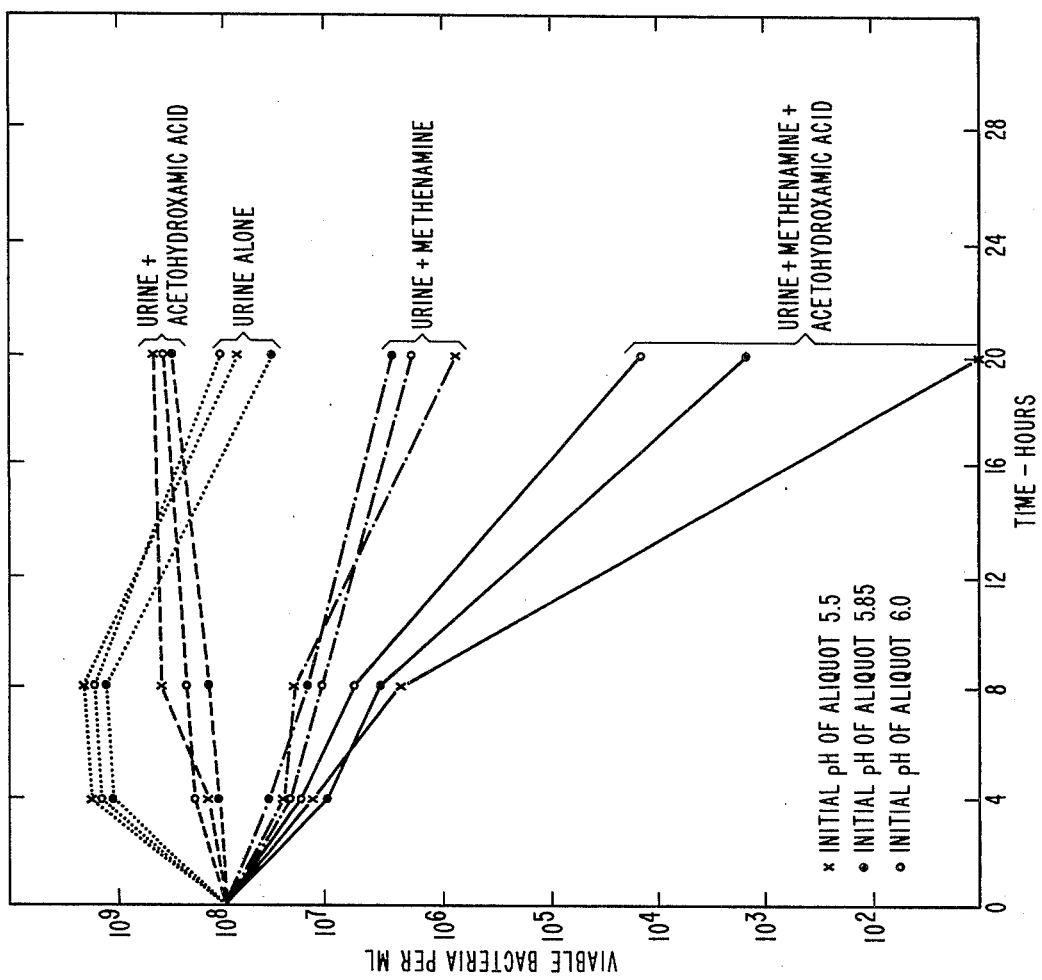
FIG. 2 is a plot of viable bacteria per milliliter vs. time in hours illustrating the synergistic anti-bacterial effect of methenamine and acetohydroxamic acid on *Proteus rettgeri;*

Elimination of Colonization and Pathogenicity of Urease Producing Bacteria Induced Urinary Tract Infection The method and composition of the present invention achieve the desired advantages over previous methods and compositions through the provision of a synergistic anti-bacterial effect exhibit with regard to urease producing bacteria through the concurrent administration of a source of methenamine and a source of hydroxamate groups, the source of hydroxamate groups being administered in an amount effective to maintain the necessary urine acidity to allow the anti-bacterial effect of the source of methenamine. The method of the present invention is applied to the treatment of patients with urinary tract infections, particularly those urinary tract infections caused by urease producing bacteria, especially those of the species Proteus.

A number of Proteus species, some of which are resistant to the highest achievable urinary concentrations of currently utilized antibiotics, have recently emerged as common hospital acquired urinary pathogens. While it has been shown that such Proteus species are susceptible to treatment with methenamine, the use of methenamine alone as an anti-bacterial agent in the treatment of urinary tract infection associated with such urease producing species has not been successful in that (1) methenamine when administered in a typical anti-bacterial dosage is not effective at an alkaline pH and the urease producing species belong to that class of bacteria which produce an alkalinization of the urine; (2) attempts to acidify the urine in the face of persisting infection associated with urease producing bacteria have not been successful; and (3) organic acids salts of methenamine, such as methenamine mandelate and methenamine hippurate have no real effect on overcoming the alkalinization of the urine in the face of urinary infections produced by urease producing bacteria.

As indicated above, the method and composition of the present invention are particularly applicable to the treatment of urinary tract infections caused by bacteria of the species Proteus. Representative examples of such Proteus species include, for example, mirabilis, vulgaris, morgani and rettgeri, all of which species of Proteus are urease producing bacteria which reduce the effective anti-bacterial action of methenamine and methenamine based compounds, when such compounds are utilized for their anti-bacterial effect in the treatment of urinary tract infections.

Source of Methenamine

The source of methenamine which is utilized as the primary anti-bacterial agent in the method and composition of the present invention can be methenamine itself or any of those compounds which combine the active methenamine nucleus with additional materials, principally formed from methenamine and an acid, especially an organic acid. In this respect, any methenamine salt with a pharmacologically acceptable acid can be employed in accordance with the present invention. For example, the active methenamine can be formulated as methenamine hippurate, methenamine mandelate or methenamine sulfosalicylate, effective urinary anti-bacterial agents. Methenamine hippurate is available from Merrell-National Labratories Division of Richard-Merrell of Cincinati, Ohio, under the name "Hiprex" and under the name "Urex" from Riker Laboratories, Inc. a subsidiary of 3M Company, Northridge, Calif. Similarly, methenamine mandelate is available from Warner-Chilcote Laboratories, Div. Warner-Lambert Company, Morris Plains, N.J. under the name "Mandelamine" methenamine sulfosalicylate is available under the name "Hexalet". Any of these forms as well as other forms of methenamine which contain the active methenamine nucleus can be utilized in accordance with the present invention to provide the required source of methenamine.

It should be apparent from the above that the examples set forth are merely exemplary of the forms which can be taken by the source of methenamine in accordance with the present invention. In this regard it is merely necessary in accordance with the present invention that the active methenamine be administered so as to allow the methenamine to exhibit its anti-bacterial effect with regard to the urinary tract infections. Accordingly, the expression "source of methenamine" as employed throughout is meant to embrace methenamine as well as all of the forms of methenamine which can effectively provide the necessary methenamine and its anti-bacterial effect.

Source of Hydroxamate Groups

Compounds which provide the active hydroxamate groups have been known prior to the present invention as specific and effective inhibitors of bacterial urease. In this regard the terminal

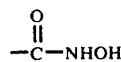

group which characterizes the group of compounds applicable in accordance with the present invention is the active site of urease inhibition and it is hypothesized that in this urease inhibition reaction two moles of the hydroxamic acid bind with one mole of urease.

Of the various compounds which contain the hydroxamate group, the four simplest aliphatic hydroxamic acids appear to possess the greatest urease inhibiting effect. These aliphatic hydroxamic acids including formohydroxamic acid, acetohydroxamic acid, propionohydroxamic acid and isobutyhydroxamic acid. Of these, acetohydroxamic acid is particularly preferred. This source of hydroxamate groups has the following characteristics:

Table 1

| | |
|---|---|
| Molecular Wt. | 75.068 |
| Structure | $\begin{array}{c} H \; O \; H \\ | \; \| \; | \\ H-C-C-N \\ | \quad\; | \\ H \quad OH \end{array}$ |
| Molar Absorbancy Index in 2% $FeCl_3$/0. | In HCL 915 |
| pKa | 9.32 |
| Melting Point | 89–91° C |

In addition to such aliphatic hydroxamic acids, other aliphatic hydroxamic acids as well as aromatic hydroxamic acids and araliphatic hydroxamic acids show the required urease inhibiting effect to be applicably employed in the method and composition of the present invention. Typical sources of hydroxamate groups falling within the foregoing classes are illustrated in an article "Effect of Acyl Residues of Hydroxamic Acids on Urease Inhibition," by K. Kobashi, Kenji Kumaki and Junichi Hase, Biochem, Biophys, Acta, 227 (1971) pages 429–441. Any of the sources of hydroxamate groups set forth in such article can be successfully employed in the method and composition of the present invention and the contents of such article are herein incorporated by reference. Accordingly, as used throughout, the expression "source of hydroxamate groups" is meant to embrace not only the preferred materials illustrated above, but in addition any of the conventional sources of hydroxamate groups which prossess the necessary urease inhibiting characteristics.

As will be appreciated hereinafter the source of hydroxamate groups utilized in accordance with the present invention, and acetohydroxamic acid in particular, show a slight anti-bacterial effect with regard to bacteria of the species Proteus; however, the anti-bacterial effect which is shown through the combination of a source of methenamine and a source of hydroxamate groups is substantially in excess of the arithmetic sum of the anti-bacterial effects of the individual compounds. Accordingly through the provision of the combination of the source of methenamine and source of hydroxamate groups a synergistic anti-bacterial effect has been created, which synergistic anti-bacterial effect allows the treatment of urinary tract infections, specifically those caused by bacteria of the species Proteus in a manner not heretofore possible with conventional treatments and compositions.

While the precise mechanism for the synergistic potentiation of the anti-bacterial effect of the sources of methenamine is not known, it appears as though this potentiation is associated with the urease inhibiting characteristic of the source of hydroxamate groups, which urease inhibiting characteristic eliminates the alkalinization of the urine associated with infections caused by bacteria of the species Proteus. In this regard since methenamine and compounds based on methenamine depend upon acidic pH and the effective anti-bacterial activity thereof is eliminated in an alkaline medium, the elimination of the alkalinization through the conjoint utilization of the source of hydroxamate groups allows the pH of the urine to be maintained in that range in which the source of methenamine is most effective as an anti-bacterial agent.

While some potentiation of the anti-bacterial effect of the source of methenamine can be explained through the urease inhibiting effect of the source of hydroxamate groups and the inhibition of the alkalinization of the urine associated with the bacteria of the species Proteus, it should be recognized that a truly unexpected synergistic effect is achieved.

Dosages and Urine Concentrations

The anti-bacterial effect of methenamine and methenamine based compounds is apparently associated with the release of formaldehyde, with the formaldehyde formed being the active anti-bacterial agent. Accordingly, the effective dosage and concentration of the source of methenamine in accordance with the present invention can be defined as that dosage or concentration which provides the desirable anti-bacterial level of formaldehyde in the urine. No precise optimum concentration of formaldehyde in the urine resulting from the release of formaldehyde from methenamine or methenamine based compound can be set forth since this will vary depending upon many factors, including the degree of infection and the particular bacterium of the species causing the infection. However, it has been discovered in accordance with the present invention that an effective anti-bacterial level of formaldehyde in the urine is achieved with a urinary concentration of methenamine within the range of about 0.05 to about 1.0 milligram per milliliter.

The particular dosage of methenamine or methenamine based compound to achieve the foregoing concentration of methenamine in the urine will depend upon many factors, including the body weight and physiology of the patient, renal activity of the patient and effectiveness of the source of methenamine to release the formaldehyde as the necessary anti-bacterial agent, this latter factor being controlled in accordance with the present invention by the conjoint administration of a source of hydroxamate groups. While the foregoing is true, generally the desired concentration of methenamine in the urine can be achieved by administering an oral dosage of methenamine or methenamine based compound of about 0.5 to about 8 grams per day, preferably 1 to 4 grams per day. It should be recognized that while such guidelines are set forth, the present invention is not in any way limited thereto since slightly greater dosages may be required in particular cases and slightly lesser dosages may be required, such as in the case of an administration of the source of methenamine and source of hydroxmate groups to children and infants. Generally, however, the desired concentration of methenamine in the urine can be achieved by administration of the above dosage.

As previously indicated, all that is necessary in accordance with the present invention to achieve the desired result is that the source of hydroxamate groups be administered in an amount effective to provide a synergistic effect with regard to activity of the source of methenamine. Here again, the dosage can be defined in terms of the desired urinary concentration of the hydroxamate groups, with the desired concentration being from about 0.05 to about 2.0 milligrams per milliliter. It is of course noted that within the foregong guidelines, dosages near the upper end of the range may be required in the initial treatment of the infection whereas dosages near the lower end of the range will be satisfactory to maintain the desired treatment. When the desired urinary concentrations are converted to oral dosages of the source of hydroxamate groups, it is generally found that a dosage of about 0.25 to about 4 grams per day of the source of hydroxamate groups will achieve the desired urinary concentration. Again, however, these dosages are merely set forth as guidelines and slightly greater and slightly lesser dosages may be administered where desired for particular purposes or where required based upon the physiology of the patient.

With regard to the ratio of the source of methenamine to the source of hydroxamate groups, no critically exists in accordance with the present invention as long as the individual components are employed in the amounts set forth above, i.e., the source of methenamine is employed in an amount effective to show the desired anti-bacterial effect and the source of hydroxamate groups is employed in an amount effective to provide a synergistic effect with respect to the anti-bacterial activity of the source of methenamine and to exhibit the desired urease inhibition. Accordingly, within these guidelines operable dosages and amounts can be selected for any particular case.

The sensitivity of methenamine and methenamine based compounds to pH is well known. In this regard methenamine for example, shows excellent release of formaldehyde at a pH of 5.0 and good release of formaldehyde at a pH of 5.5. At a pH of 6.0 the release of formaldehyde is generally adequate for the treatment of most urinary tract infections, but as the pH of the urine reaches 6.5 insufficient conversion and release of formaldehyde is achieved and the anti-bacterial effect of the methenamine is totally diminished. Because of this problem, the art has long sought a mechanism by which the effective anti-bacterial characteristics of methenamine can be achieved even in the face of urease producing bacteria, this now being achieved through the provision of the present invention comprising the conjoint administration of a source of methenamine and a source of hydroxamate groups.

The form of the compounds administered in accordance with the present invention can be any of the conventially utilized for the administratiion of pharmacologically effective compounds, orally or parenterally. Thus, for example, the source of methenamine and the source of hydroxamate groups can be administered in a liquid form utilizing a conventional alcohol or similar vehicle or alternatively the source of methenamine and source of hydroxamate groups can be administered in the form of tablets or in the form of capsules, utilizing conventional fillers, excipients, etc. to provide the necessary form of the desired dosages.

Elimination of Pathogenicity of Urease Producing Bacteria Induced Urinary Tract Infections Various investigators have put forward the hypothesis that urease is responsible for the ability of Proteus and similar bacteria which are urease producing bacteria to cause urinary tract infections. This hypothesis is supported by the fact that bacteria of the Proteus species rarely cause infections outside of the urinary tract, although they are very frequent pathogens in the urinary tract. This is apparently due to the fact that urine is the only substance in the body that contains substantial amounts of urea, i.e., sufficient urea that when broken down by urease a sufficient amount of ammonia is generated to cause alkalinization. The pathogenicity as referred to herein relates to the tissue damage that results when urease producing bacteria infect the urinary tract and is distinguishable from the colonization by the bacteria which can exist without damage to tissues.

Since infection can be defined as damage to tissue by micro-organisms and always implies some host response, such as an outpouring of white blood cells, unless of course the host has been pretreated in a manner to prevent this response, the elimination of the pathogenicity of the infection can effectively eliminate the infection itself while allowing the colonization of the bacteria, which colonization does not itself cause tissue damage. This has been achieved in accordance with the present invention by administering the urease inhibiting compounds previously described, i.e., source of hydroxamate groups, and acetohydroxamic acid in particular. These compounds effectively inhibit the urease which confers pathogenicity of the Proteus species of bacteria. By inhibiting the urease in this manner and by eliminating the pathogenicity of the infection, the infection itself is eliminated and tissue damage prevented, though colonization of the bacteria may persist. This is achieved in accordance with the present invention without the simultaneous addition of an antibacterial agent, such as a source of methenamine, which is effective to eliminate the colonization of the urease producing bacteria. Accordingly, this aspect of the present invention provides for the administration of only the source of hydroxamate groups, with an associated elimination of the pathogenicity of the infection, absent elimination of bacteria colonization.

As will be appreciated from the later present examples, by administering only the source of hydroxamate groups it is possible to effectively eliminate tissue damage caused by urease producing bacteria by inhibiting the action of the pathogenic factor, namely urease, notwithstanding the fact that colonization of the bacteria is not eliminated. In this respect the colonization of the bacteria which continues does not produce adverse effects, such as tissue damage, since the pathogenic agent responsible for the infection and associated tissue damage is eliminated. Accordingly, the present invention, by administration of only the active urease inhibiting compound, i.e., source of hydroxamate groups, is a simple and efficient means of treating and eliminating urinary tract infections, specifically those urinary tract infections associated with urease producing bacteria, especially those of the species Proteus.

The foregoing discussion involves a unique approach to the treatment of infections in that the approach does not necessarily aim toward elimination of the bacteria with which the infection is associated but rather toward blocking the effect of the pathogenic agent produced by the bacteria, whereby the tissue damage induced by the bacteria and/or bacterial agent is stopped. This phenomenon provides a new simplified approach to the treatment of infection.

In connection with this approach to the treatment of infections it is pointed out that the dosages and forms of the active urease inhibiting compound, i.e., source of hydroxamate groups are the same as previously set forth in connection with the combined administration of a source of hydroxamate groups and a source of methenamine. The amount of hydroxamate groups introduced into the system should be that amount effective to produce the desired urease inhibiting effect, such that the active pathogenic agent, i.e., urease can be inhibited and tissue damages associated with this pathogenic agent stopped.

Stone Dissolution

It is a general contention that bacterial infection of the urine may cause urinary stone formation and there is considerable data establishing the cause and effect relationship between urea-splitting urinary infections and struvite and calcium apatite stone formation. It is hypothesized that urease producing bacteria cause stone formation due to the alkalinity produced by the hydrolysis of urea. Consideration has been given to dissolving of the urinary stones since, as previously noted, the bacteria within the stone can reinfect the urinary tract.

It has been discovered in accordance with the present invention that urease producing bacteria promote stone formation by way of the enzyme urease. Moreover, it has been discovered in accordance with the present invention that by administering to a person suffering from infected urinary stones an effective urease inhibiting amount of an inhibitor, such as the sources of hydroxamate groups previously described, and acetohydroxamic acid in particular, it is possible to maintain the urine at a physiological pH and thereby produce an environment effective for the dissolution of urinary stones.

Sterile urine from patients not suffering from urinary tract infections is usually acidic and under-saturated with respect to struvite and apatite crystals. Due to such undersaturation such urine will dissolve struvite and apatite stones. By preventing alkalinization and maintaining urine in a state of under-saturation, despite the presence of urease producing bacteria, it is possible in accordance with the present invention to provide a urine with a physiological pH that will dissolve such struvite and apatite crystals in the form of urinary tract stones. Accordingly, the method of the present invention involves administering an effective urease inhibiting amount of a source of hydroxamate groups to a patent suffering infection from urinary tract stones for the purpose of dissolving such stones.

With respect to this embodiment of the present invention the types of compound effective to dissolve the stones are the same compounds previously described. In addition, the dosages set forth previously with regard to such introduction of a source of hydroxamate groups are essentially the same as employed in this embodiment of the present invention with respect to dissolving struvite and apatite stones. In this embodiment the source of hydroxamate groups can be administered either alone or in combination with a source of methenamine to both dissolve the stones and eliminate the colonization of the urease producing bacteria.

The methods and composition of the present invention will now be illustrated by way of specific examples. It should be recognized that these examples are presented solely for the purpose of illustration and the present invention cannot under any circumstances be deemed limited thereby.

EXAMPLE 1

Static studies were conducted to illustrate the synergistic effect achieved in accordance with the present invention through the combined employment of a source of methenamine, i.e., methenamine itself and a source of hydroxamate groups, i.e., acetohydroxamic acid.

In order to achieve reproducibility of results with large quantities or urine required for these studies a synthetic urine was formulated based on the proportion of solutes found in the urine from normal human subjects. The composition of such urine was as follows:

COMPOSITION OF SYNTHETIC URINE

| Compound | Gm/L | Concentration/L |
|---|---|---|
| $CaCl_2 \cdot 2H_2O$ | 0.65 | Ca - 4.3mM |
| $MgCl_2 \cdot 6H_2O$ | 0.651 | Mg - 3.2mM |
| NaCl | 4.6 | |
| $Na_2SO_4$ | 2.3 | $SO_4$ - 16mM |
| $Na_3$ Citrate $\cdot 2H_2O$ | 0.65 | Citrate - 2.3mM |
| $Na_2$ Oxalate | 0.020 | Oxalate - .149mM |
| $KH_2PO_4$ | 2.8 | $PO_2$ - 20.5mM |
| KCl | 1.6 | |
| $NH_4Cl$ | 1.0 | $NH_4$ - 19mEq |
| Urea | 25.0 | |
| Creatinine | 1.1 | |
| | | Total Na = 118mEq |
| | | Total K = 42mEq |

Brain heart infusion (BHI) broth in a final concentration of 5% was added to support bacterial growth. The pH of the synthetic urine prior to addition of the BHI broth was 5.7 – 5.8. It was found that the growth of the Proteus bacteria in the synthetic urine an the alkalinization of the synthetic urine utilized proceeded at approximately the same rate as in random human urine from normal subjects.

In these tests the methenamine was utilized in a final concentration of 0.9 milligrams per milliliter. Acetohydroxamic acid was synthesized by the procedure set forth in "PREPARATION AND SOME PROPERTIES OF STABLE AND CARBON −14 AND TRITIUM-LABELED SHORT-CHAIN ALIPHATIC HYROXAMIC ACIDS", Fishbein, W. N., J. J. Dally and C. L. Streeter, 1969, *Analytical BioChem* 28:13–21. The acetohydroxamic acid which was synthesized was added to the urine to provide a concentration of 1.9 mg/ml. These concentrations which were selected in the static studies were concentrations which would be achievable in the urine of patients with normal renal function.

In accordance with these studies methenamine alone, the acetohydroxamic acid alone and both methenamine and acetohydroxamic acid were added to the synthetic urine in the above concentrations and aliquots of the three types of samples, as well as the synergistic urine alone, were adjusted at 0.1 pH unit intervals from 5.6 to 6.1 by titration with 1 N HCl or 1 N NaOH. At each pH level a set of four tubes was obtained, with these tubes being as follows:
1. Urine alone (control);
2. Urine plus methenamine;
3. Urine plus acetohydroxamic acid; and
4. Urine plus acetohyroxamic acid plus methenamine.

Bacteria of the species Proteus were added to yeild $10^7$ organisms per milliliter and each of the tubes was incubated at 37° centigrade. At varying time intervals aliquots were removed for pH determination and bacterial enumeration by serial tenfold dilution.

As a result of such static tests is was found that the growth of the Proteus bacteria in the synthetic urine alone caused the pH to rise to greater that pH 8.0 within 8 hours. This illustrates the effect of urease production by Proteus bacteria on the pH of urine. It was further found that the rate of alkalinization varied with the bacterial strain but was unrelated to the initial pH.

Figure 1:
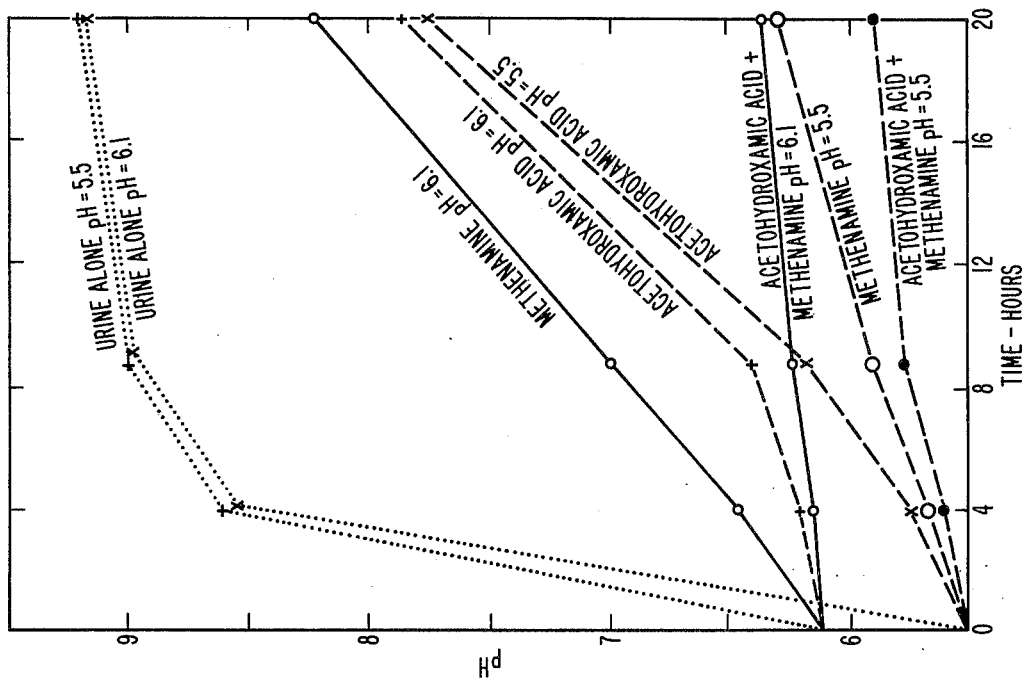
FIG. 1 is a plot of pH vs. time in hours illustrating the effectiveness of the combination of methenamine and acetohydroxamic acid on the alkalinization of urine by the growth of *Proteus retteri;*

With respect to the samples containing synthetic urine and the acetohydroxamic acid it was found that the acetohydroxamic acid inhibited alkalinizaton for the first eight hours, but its effects as a urease inhibitor were overcome within 24 hours by bacterial poliferation leading to an alkaline pH. With regard to the samples containing synthetic urine and methenamine it was found that the anti-bacterial effect of methenamine was dependent upon the starting pH. When the initial pH was less than 5.3 only a slight upward drift was observed, consistent with secondary metabolic reactions in dead and dying bacterial cells. At a pH greater than 6.5 the presence of methenamine did not alter progressive alkalinization. Between these extremes alkalinization was inhibited in proportion to the initial urine acidity. When methenamine and acetohydroxamic acid were combined in the synthetic urine, a synergistic effect was exhibited, with alkalinization being inhibited to approximately the same degree between pH 5.5 and 6.1 with all of the Proteus species studied, i.e., *Proteus mirabilis*, *Proteus vulgaris*, *Proteus morgani* and *Proteus rettgeri*. The synergistic effect on the alkalinization of urine by the growth of *Proteus rettgeri* can be seen in FIG. 1.

With regard to the alkalinization of urine by the growth of *Proteus rettgeri* a synergistic effect is achieved when methenamine and acetohydroxamic acid are combined in the synthetic urine, in that alkalinization is inhibited through the combination to about the same degree between pH 5.1 and 6.1 and no undesirable alkalinization is seen. This is compared to the case of urine plus methenamine alone and urine plus acetohydroxamic acid alone.

The synergistic effect achieved in accordance with the present invention with regard to bacterial growth can be seen by reference to FIG. 2 which plots the viable bacteria per milliliter against time in hours, the bacteria being *Proteus rettgeri*. Results similar to those of FIG. 2 were seen for the other Proteus species studied.

As seen from FIG. 2 bacterial counts in urine rose to greater than $10^8$ per milliliter within four hours. The acetohydroxamic acid exerted a slight bacteriostatic effect; however, within eight to eighteen hours the number of bacteria approached $10^8$ per milliliter. The anti-bacterial effect on the methenamine was proportional to the initial pH and as illustrated in FIG. 2 the acetohydroxamic acid potentiated the bactericidal effect of methenamine at every pH between 5.5 and 6.1 and this synergistic effect was seen for all Proteus species studied. It can be seen from FIG. 2 that the bacterial effect achieved through the combined presence of methenamine and acetohydroxamic acid is far greater than the bacterial effects shown for methenamine alone, acetohydroxamic acid alone or what would be expected from the arithmetic sum of the two.

EXAMPLE 2

Dynamic studies were conducted to further illustrate the synergistic effect associated with the combined presence of a source of methenamine, i.e., methenamine itself and a source of hyroxamate groups, i.e., acetohydroxamic acid in the urine.

Utilizing the same synergistic urine as in example 1, a dynamic system was designated to resemble a Proteus infected human bladder. Utilizing a multicassetts roller pump, urine of a pH of 5.85 was pumped at 40 milliliters per hour from three reservoir flasks into three reaction chambers. The synthetic urine in flask 1 contained no acetohydroxamic acid, while the urine in flask 2 and 3 contained 1.9 milligrams acetohydroxamic acid per milliliter. An aqueous solution of 18 milligrams per milliliter of methenamine at a pH of 7.5 was pumped into reaction chambers 1 and 3 at a rate of two milliliters per hour yielding a final concentration of methenamine of 0.9 milligrams per milliliter. As a result of this reaction chamber 1 contained methenamine, reaction chamber 2 contained acetohydroxamic acid and reaction chamber 3 contained methenamine plus acetohydroxamic acid. A control containing urine alone was not carried out in the dynamic study since preliminary investigations had shown that the 0.9 milligrams per millimeter methenamine affected growth of Proteus and alkalinization of urine only slightly in this dynamic system when compared to the synthetic urine alone. The reaction chambers contained gently rotating magnetic stirrers and were kept in a warm bath at 37° C.

At the start of this dynamic experiment 5 milliliters of urine at a pH of 8.9 containing $10^7$ Proteus per milliliter were added to each reaction chamber. At 4 – 6 hour intervals the volume of urine in each reaction chamber was recorded, the pH of each reaction chamber was determined and serial dilutions were carried out for bacterial enumeration. The reaction chambers were then emptied leaving a residual urine volume of 5 milliliters.

Figure 3:
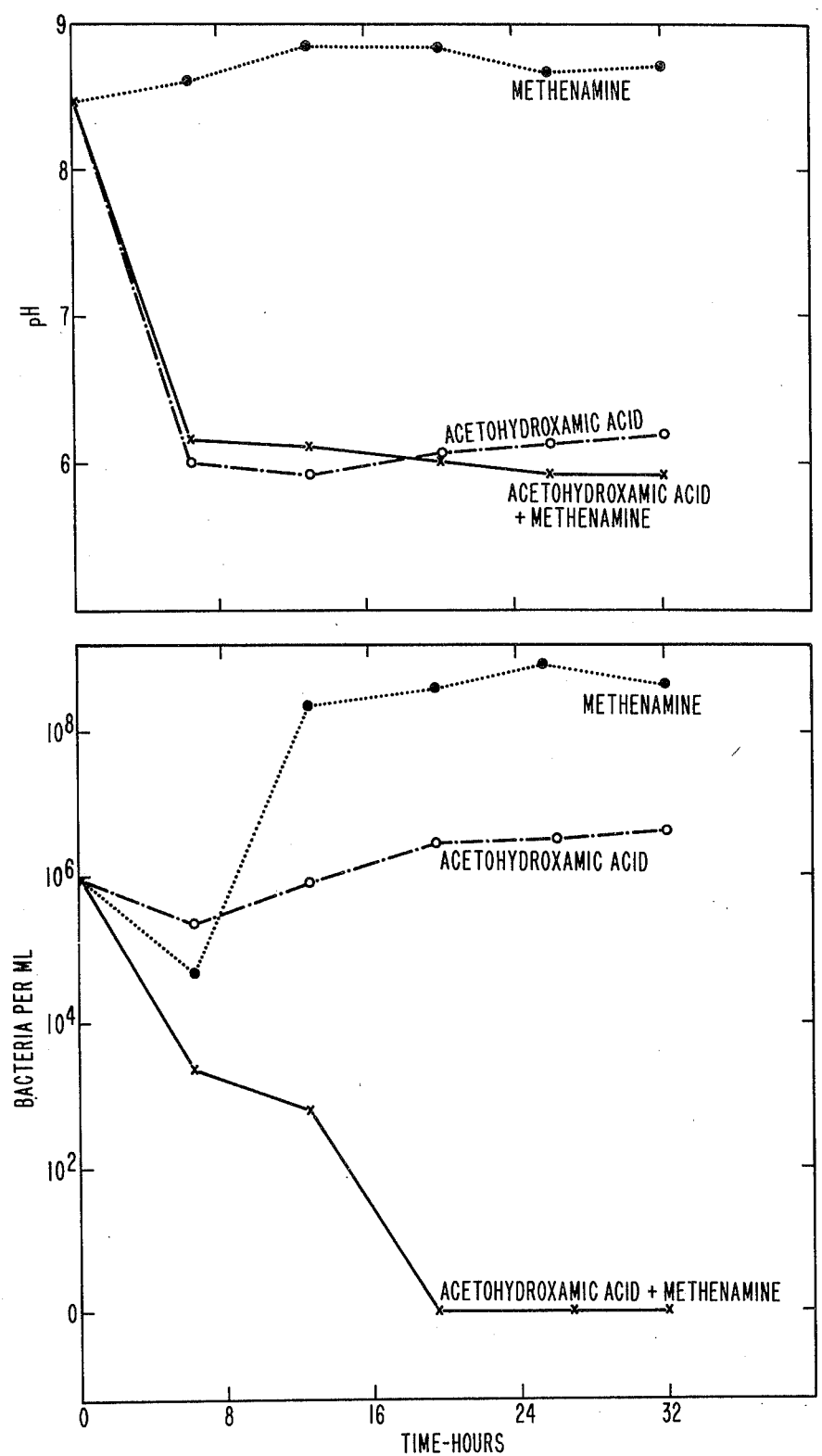
FIG. 3 is a plot of bacteria per milliliter and pH vs. time in hours illustrating the effect of methanamine and acetohydroxamic acid in a dynamic study with *Proteus rettgeri;*

The results which were achieved in this dynamic test are illustrated in FIG. 3, which sets forth the results with regard to the dynamic study with *Proteus rettgeri*. Similar results were achieved with each of the Proteus bacteria studied.

As seen in FIG. 3, in the urine containing methenamine, at the end of each four to eight hour period the pH always exceeded 8.5, i.e., a pH at which there is no anti-bacterial effect of methenamine. The number of bacteria per milliliter fell slightly during the first six hours, but by the end of the second time period the colony count had risen to greater than $10^7$ per milliliter where it remained throughout the study. However, in the presence of acetohydroxamic acid alkalinization of Proteus was inhibited and the pH fell to 5.85 – 6.1 within the first six hours and remained in that range throughout the study. The acetohydroxamic acid exhibits a minor bacteriostatic effect maintaining the number of bacteria between $10^5$ and $10^7$ per milliliter. In the presence of both the acetohydroxamic acid and methenamine, the pH remained acid throughout and there was a steady decline in colony count resulting in sterilization of the system within 24 – 48 hours. This illustrates that the acetohydroxamic acid and methenamine together exert a synergistic effect against urease producing bacteria, especially those of the Proteus species.

EXAMPLE 3

In this example in vitro investigations were carried out using a static-dynamic system delineating (1) bacteriostatic dose-response relation for methenamine against Proteus, and (2) a synergistic bacteriostatic dose-response relation for methenamine and acetohydroxamic acid against Proteus.

Experimental Model

This experiment model to be described seeks to demonstrate sequential dilution of growth inhibited bacteria at 6 hour intervals.

Tubes containing 10 ml synthetic urine was inoculated with *Proteus mirabilis*, *Proteus rettgeri* or *Proteus morgani* to give a final bacterial concentration of $10^4$ – $10^7$ per ml. Separate tubes contained (1) urine only, (2) urine and acetohydroxamic acid, and (3) urine and methenamine, (4) urine, acetohydroxamic acid and methenamine. The tubes were placed in a bacteriological incubator at 37° C. At 6 hour intervals 100 microliters of urine were withdrawn from each tube and the tube was discarded. The 100 microliter aliquot was added to 10 ml of synthetic urine which contained the same concentration of constituents (except bacteria) as the initial tubes. Incubation of the tubes at 37° and sequential dilutions were made a 6 hour intervals for 24 hours. The variables for each of eight experiments are detailed in Table 2.

TABLE 2

EXPERIMENTAL VARIABLES

| Expt. | Bacteria | Initial Bacterial Inoculum cfu/ml | Urine pH* | AHA conc.* mg/ml | No. 1 Meth. conc.* mg/ml | No. 2 Meth. conc.* mg/ml |
|---|---|---|---|---|---|---|
| A | P. mirabilis | 5 × $10^4$ | 5.9 | 0.2 | 0.05 | 0.1 |
| B | P. mirabilis | 3 × $10^5$ | 5.9 | 0.2 | 0.05 | 0.1 |
| C | P. mirabilis | 3 × $10^6$ | 5.9 | 0.2 | 0.05 | 0.1 |
| D | P. mirabilis | 5 × $10^7$ | 5.9 | 0.2 | 0.05 | 0.1 |
| E | P. mirabilis | 5 × $10^6$ | 5.9 | 0.2 | 0.1 | 0.2 |
| F | P. mirabilis | 8 × $10^7$ | 5.9 | 0.2 | 0.1 | 0.2 |
| G | P. mirabilis | 3 × $10^6$ | 5.9 | 0.1 | 0.05 | 0.1 |
| H | P. mirabilis | 6 × $10^7$ | 5.9 | 0.1 | 0.05 | 0.1 |
| I | P. mirabilis | 5 × $10^7$ | 6.5 | 0.1, 0.05 | 1.0 | 0.5 |
| J | P. mirabilis | 1 × $10^8$ | 7.0 | 0.1, 0.05 | 1.0 | 0.5, 0.2 |
| K | P. rettgeri | 7 × $10^7$ | 5.9 | 0.05 | 0.05 | 0.1 |
| L | P. morgani | 1 × $10^8$ | 5.9 | 0.1, 0.05 | 0.05, 0.01 | 0.1 |

*The initial pH and concentration of constitutents was identical in all tubes at the beginning of each six hour incubation.

Bacterial colony forming units (cfu) and urine pH were determined at the beginning and at the completion of each six hour incubation. The cfu units present after six hours of incubation are graphed in FIGS. 4–15. Bacteriostasis was demonstrated by a decline in the number of cfu after each incubation. When bacteriostatis was absent, the number of cfu after six hours of incubation was equal to or greater than the number of cfu at the beginning of incubation.

Bacteria

A strain of *Proteus mirabilis* isolated from the urine of patients with urinary tract infections was used in most experiments. Overnight growth in brain heart infusion (BHI) broth regularly produced $10^9$ cfu/ml. The overnight culture was centrifuged at 3000 rpm for 20 minutes. The supernatant was discharged, and the bacterial pellet was resuspended in an equal volume of synthetic urine. The bacteria were resuspended in synthetic urine to prevent differences in pH as the bacteria were inoculated into tubes of synthetic urine. The bacterial suspension was inoculated into 10 ml of synthetic urine to achieve final concentrations of $10^4 - 10^7$ cfu/ml. Bacteria were counted by making serial ten-fold dilutions following which 0.1 ml aliquots were streaked onto MacConkey's agar.

Urine

The urine utilized was a synthetic urine as illustrated in Example 1.

Methenamine and Acetohydroxamic Acid

Methenamine was used in final concentrations from 0.05 mg/ml to 0.20 mg/ml. Acetohydroxamic acid was synthesized in the same manner as described in Example 1 and was added to give final concentrations of 0.05–0.20 mg/ml. The results are illustrated in FIGS. 4–15 which relates respectively to Experiment A-L of Table 2. Each of FIGS. 4–15 represents colony forming units (cfu) present at the completion of six hour incubations. 100-fold dilutions were made prior to initiating subsequent six hour incubations. Each figure also includes a line representative of theoretically perfect bacteriostasis.

When bacteriostatis was absent, bacteria grew rapidly, usually reaching equal to or greater than $10^8$ per ml within the first six hours of incubation. Significant bacteriostasis resulted in a reduced bacterial count (cfu) with each subsequent dilution.

Acetohydroxamic Acid Only

Acetohydroxamic acid at a concentration of $\approx 0.9$ mg/ml exerted no bacteriostatic effect. The acetohydroxamic acid data was omitted from Table 2 and FIGS. 4–15 in an effort to simplify the presentation.

Methenamine Only

Figure 5:
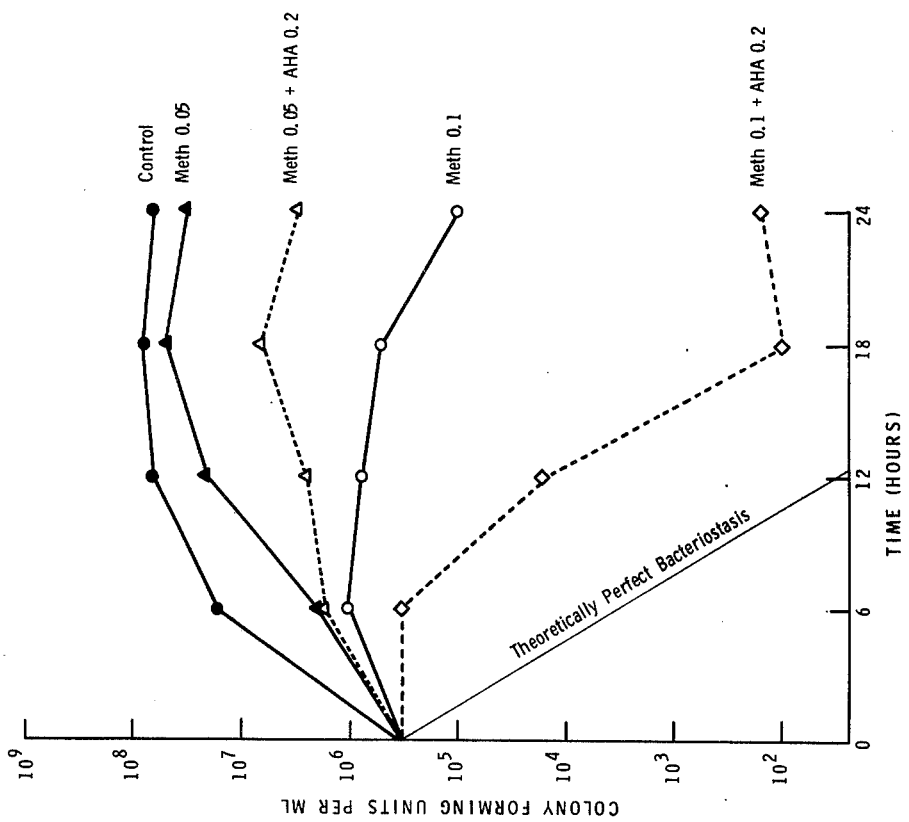
Figure 4:
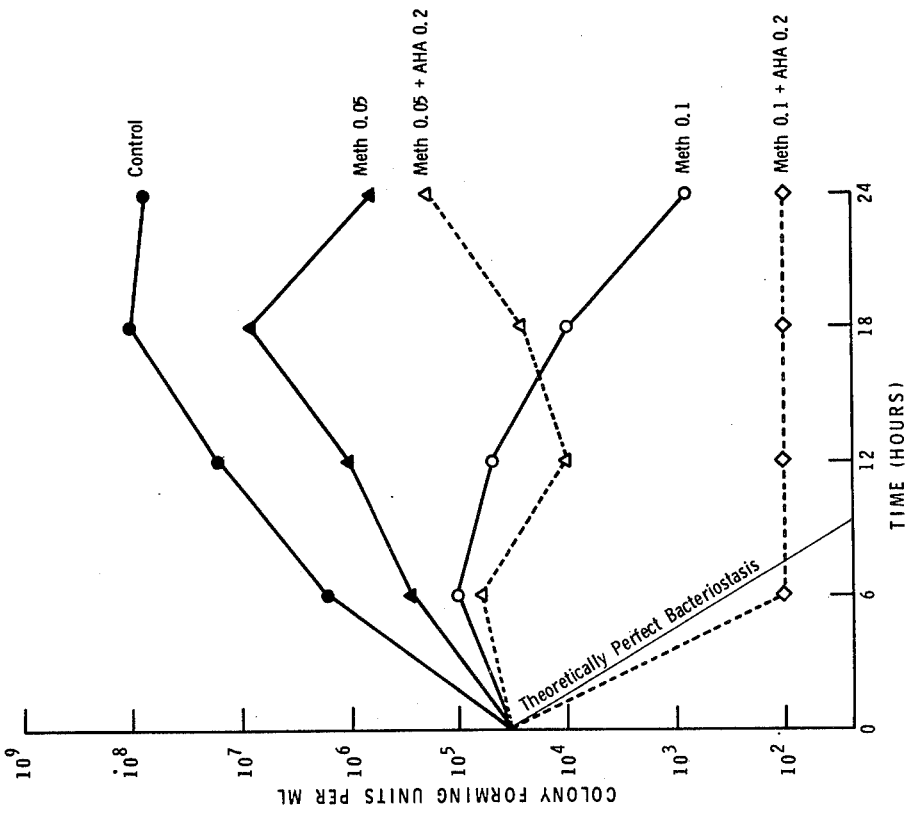
Figure 7:
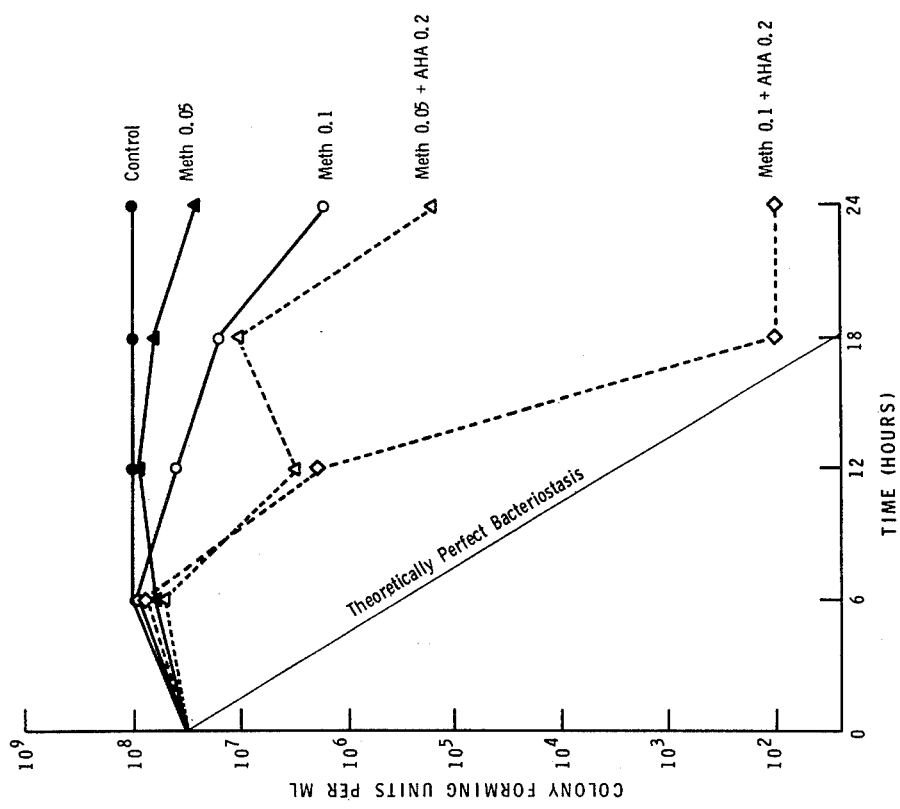
Figure 6:
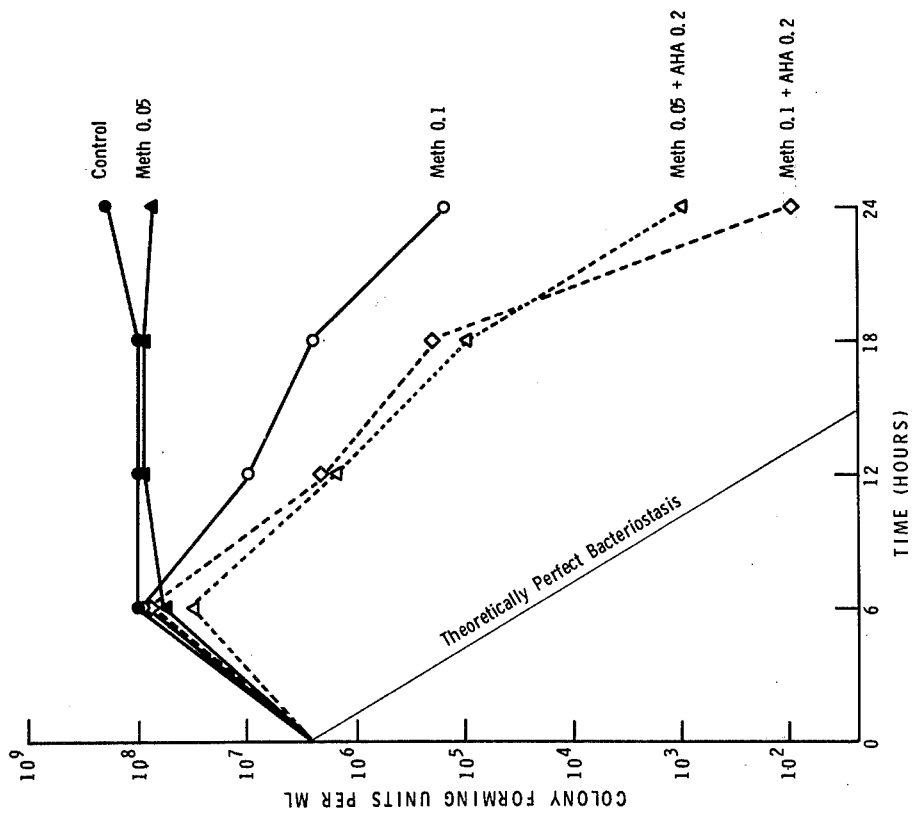
Figure 11:
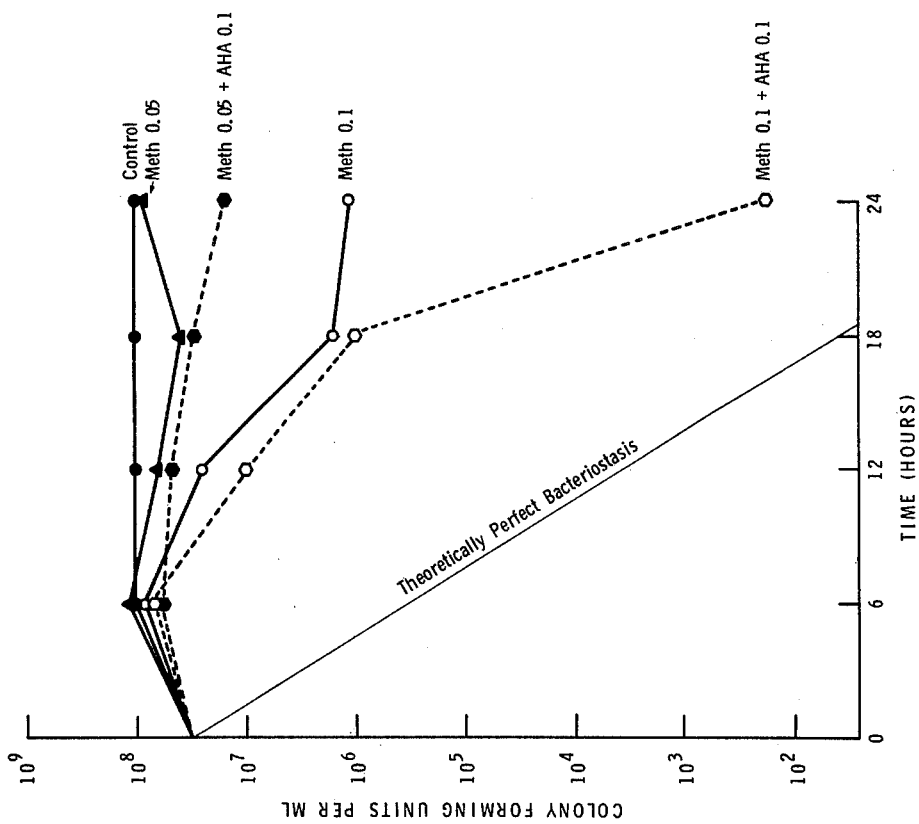
Figure 10:
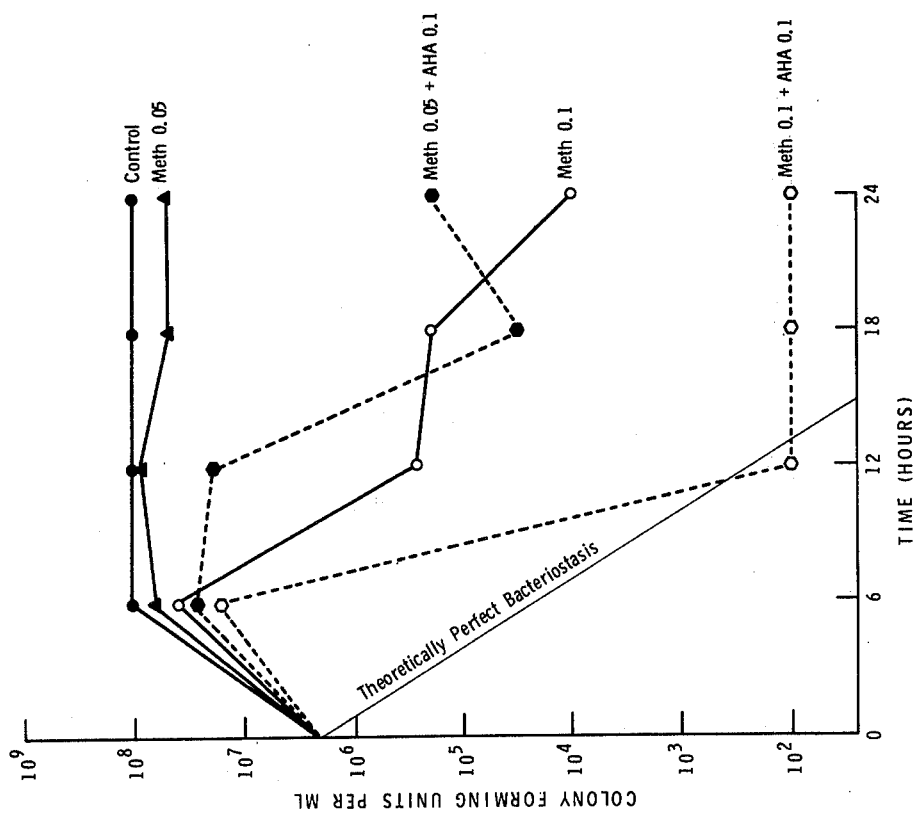
Figure 13:
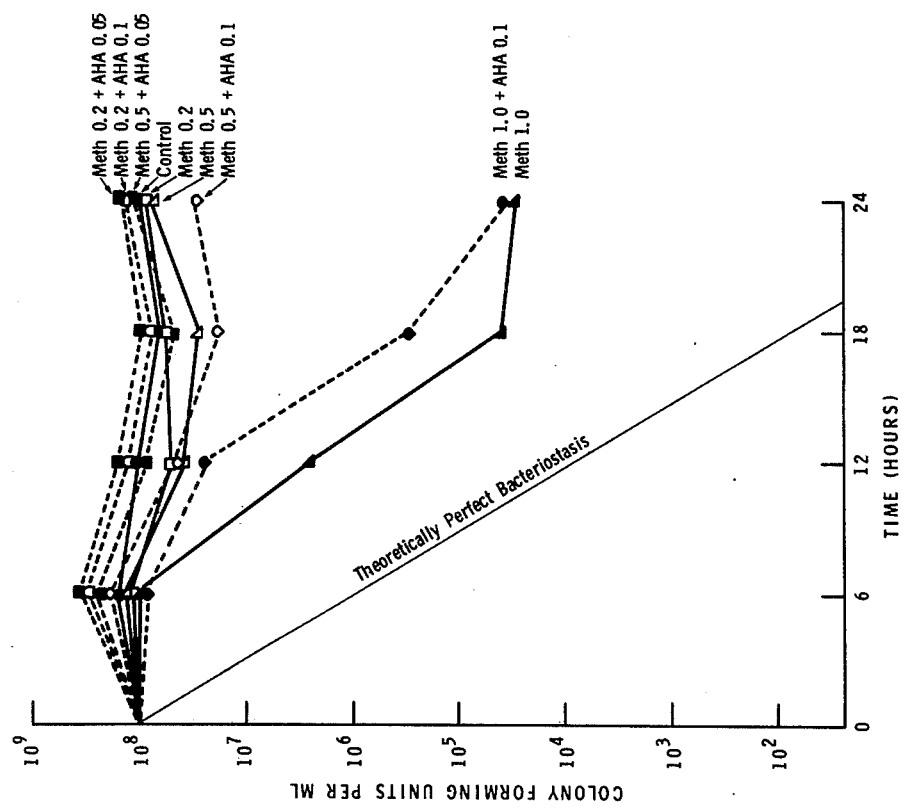
Figure 12:
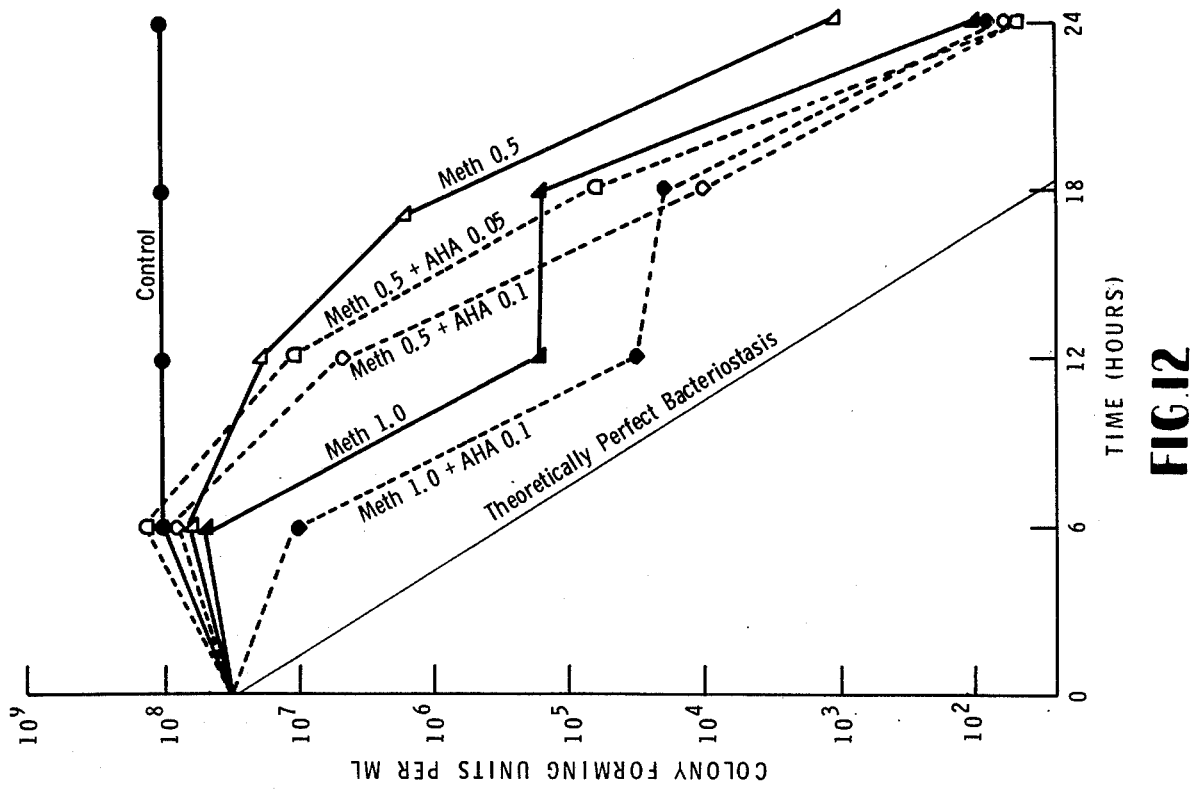

Experiments A and B suggest that 0.05 mg/ml methenamine has some bacteriostatic activity in urine at pH 5.9 against small concentrations of *Proteus mirabilis* ($10^4$/ml and $10^5$/ml) (FIGS. 4, 5). Experiments C through H demonstrate no bacteriostasis by 0.05 mg/ml methenamine against larger concentrations of bacteria ($\geq 10^6$/ml *Proteus*).

All experiments performed in acidic urine demonstrate bacteriostasis by 0.1 mg/ml methenamine (FIGS. 4–7, 10 and 11. Experiments E and F (FIGS. 8, 9) demonstrate bacteriostasis by 0.2 mg/ml methemanine. These concentrations of methenamine were bacteriostatic against all concentrations of Proteus ($10^4 - 10^7$ per ml). Methenamine at a concentration of 0.2 mg/ml consistently exerted a greater bacteriostatic effect than did methenamine 0.1 mg/ml (FIGS. 8, 9).

Methenamine and Acetohydroxamic Acid

In every experiment involving acidic urine the combination of methenamine and acetohydroxamic acid exerted a more pronounced bacteriostatic effect than did methenamine alone (FIGS. 4–11, 14 and 15). In experiment A, 0.2 mg/ml acetohydroxamic acid enhanced the mild bacteriostatic effect of 0.05 mg/ml methenamine against small concentrations of bacteria. The 0.05 mg/ml methenamine had little or no bacteriostatic activity against large concentrations of bacteria ($\geq 10^6$ *Proteus*/ml), the combination of methenamine 0.05 mg/ml and acetohydroxamic acid 0.2 mg/ml did exert a reproducible bacteriostatic effect (FIGS. 4–7).

In experiments K and L (FIGS. 14 and 15) 0.05 mg/ml acetohydroxamic acid potentiated the bacteriostatic effect of 0.05 mg/ml methenamine. Methenamine and the acetohydroxamic acid - methenamine combination were much less bacteriostatic in alkaline urine (FIGS. 12 and 13) than in acidic urine.

EXAMPLE 4

This example was carried out using a dynamic model as described in connection with Example 2. This model more closely approximates the dynamics of the urinary tract, i.e., residual urine after simulated voiding is approximately 5 ml and bacteria may adhere to particulate matter or to the walls of the container.

Bacteria

Proteus species, isolated from the urine of patients with known urinary infection, were maintained in the laboratory by monthly transfer on agar slants. These organisms grew to about $10^9$ colony forming units (cfu) per ml after overnight growth at 37° C in brain heart infusion broth (BHI). Bacteria were counted by carrying out serial tenfold dilutions and plating 0.01 ml aliquots onto BHI agar (enriched with 2% additional agar to prevent bacterial swarming) and MacConkey' agar.

Synthetic urine.

Synthetic urine formulated as previously described (Ex. 1) was used. The pH of this synthetic urine was 5.85.

Acetohydroxamic Acid

Acetohydroxamic acid was synthesized as described in Example 1; the chemical preparations used for these studies were 98–99% pure.

Ammonia determinations

The concentration of ammonia in urine was measured using an Orion ammonia electrode (Orion Instruments, electrode No. 95–10).

In this dynamic system urine with or without acetohydroxamic acid was pumped at 48 ml/hr from reservoirs via an auto-analyzer pump into reaction chambers which were incubated in a shaking water bath at 37° C. Methenamine from a separate reservoir at an alkaline pH was added at 1.8 ml/hr into some of the reaction chambers to yield final concentrations ranging from 0.1 to 0.5 mg/ml. Every six hours the reaction chambers were emptied except for a 5 ml residual, and the sequence was repeated. In these experiments the pH, ammonia concentration and cfu per ml urine were determined for each reaction chamber at the end of each six hour period.

Figure 17:
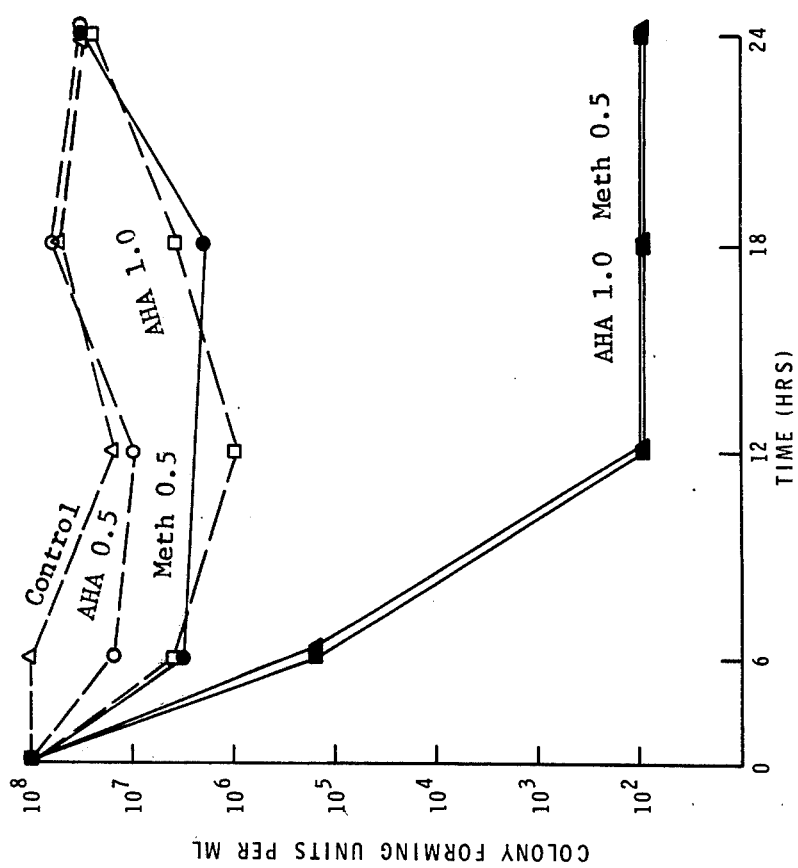
* and FIG. 17 is a cumulative plot of methenamine concentration vs. colony forming units per milliter for six dynamic system equipment with *Proteus mirabilis.*
Figure 16:
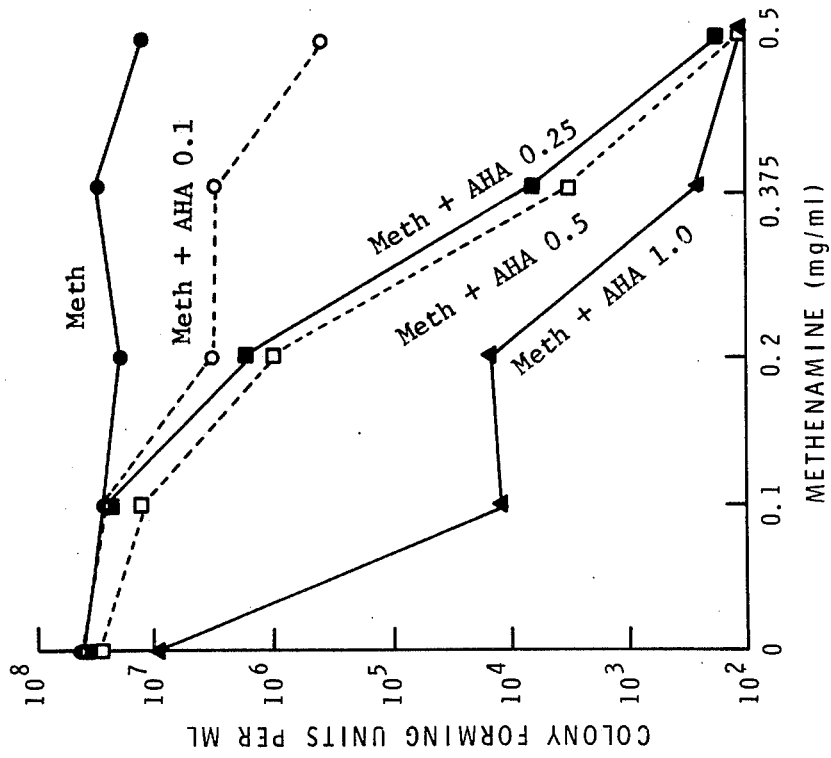
FIG. 16 is a plot of time in hours vs. colony forming units per milliliter for a typical dynamic system experiment with *Proteus marabilis.

In this dynamic system acetohydroxamic acid consistently potentiated the anti-bacterial activity of methenamine. Results of a representative study using 0.5 mg/ml methenamine and 0.5 or 1.0 mg/ml acetohydroxamic acid are shown in FIG. 16. Methenamine alone and the higher concentration of acetohydroxamic acic slightly inhibited bacterial growth. Either concentration of acetohyroxamic acid together with methenamine caused a marked decline in cfu; as has been shown for methenamine in other systems, an actual bactericidal effect seems to have been observed. In this study 1 mg/ml acetohydroxamic acid maintained the pH at normal levels without methenamine being present. The initial tendency for the pH to neutralize in the presence of methenamine alone was overcome by the end of 18–24 hours. With lower concentrations of methenamine the pH rapidly became alkaline and remained so throughout. The presence of acetohydroxamic acid and methenamine together kept the pH in a normal range. Ammonia concentrations closely followed pH in all the studies that were done. In this dynamic model synergy was observed for all concentrations $\geq$ 0.2 mg/ml acetohydroxamic acid and $\geq$ 0.2 mg/ml methenamine. As little as 0.1 mg/ml methenamine was bacteriostatic in the presence of 1.0 mg/ml acetohydroxamic acid. Cumulative results of all studies which indicate bacterial counts at the end of 18 hours in each individual experiment are shown in FIG. 17. In all of these experiments prevention of alkalinization by acetohydroxamic acid and methenamine together could be demonstrated with slightly lower concentrations of both compounds than those required to demonstrate bacteriostasis.

EXAMPLE 5

This example was carried out to illustrate the effectiveness of administering a source of hydroxamate groups, e.g., acetohydroxamic acid in eliminating the pathogenicity of urinary tract infections and in dissolving or reducing infected bladder stones.

The formation of infected bladder stones was induced in 250 gram male Sprague-Dawley rats, according to the method described in "Experimental Urolithiasis VIII — Furadantin in Treatment of Experimental Proteus Infection with Stone Formation" C. W. Vermuelen and R. Goetz, *Journal of Urology*, 72:99, 1954. Rats wer anesthetized with ether and the abdominal wall swabbed with 70% ethyl alcohol. The urinary bladder was entered through a small suprapubic incision. Zinc discs, 6 mm. in diameter, were dipped into a saline suspension containing $10^7$ *Proteus mirabilis* per ml (infective discs) and immediately inserted into the bladder. Discs handled in this fashion carried $10^5 \pm 15\%$ organisms. The bladder was closed with a single pursestring suture of 3–0 chromic catgut, and the skin was approximated with metallic clips. All animals were fasted overnight following the surgical procedure and resumed their usual diet the following day.

Rats were housed individually in stainless steel metabolic cages and were fed Purina Rat Chow pellets ad lib. Fluid was given in stainless steel cups as a solution of 5–20% sucrose in water.

Treatment with acetohydroxamic acid was begun in half the rats the day after surgery. These animals were offered 150 mg. of acetohydroxamic acid daily in 20% sucrose-cola solution of which they ingested an average of 100 mg. The concentration of acetohydroxamic acid in their urine varied from 0.3 to 7.8 mg/ml (means 2.88 mg/ml). Control animals for this study received no acetohydroxamic acid. Their fluid intake was adjusted to equal that of the acetohydroxamic acid treated group by pair watering. All animals were sacrificed on the seventh day.

The urine pH in the control animals was persistently alkaline after the *Proteus mirabilis* urinary infection was induced. Urine cultures obtained at autopsy grew *Proteus mirabilis* $> 10^5$ organisms/ml and bladder stone formation was abundant (mean 52.1 ± 27 mg) in all control rats except for one, which had sterile, acidic urine. This animal appeared to have eliminated all signs of infection spontaneously. All of the infected control animals had gross evidence of pyelonephritis at autopsy. Most had renal and/or perinephric abscesses and intrarenal stone formation. Histologic examination demonstrated the presence of acute parenchymal inflammation with abscesses in all cases, except the one animal with sterile urine which had normal kidneys.

In contrast, the urine pH of the acetohydroxamic acid treated animals remained in the normal range. Urine obtained at autopsy contained greater than $10^5$ *Proteus misabilis* per ml but bladder stone formation was minimal. Differences in mean urine pH and stone formation, between the control and acetohydroxamic acid treated groups were satistically significant (P.<0.01). Although all acetohydroxamic acid treated rats had abundant *Proteus mirabilis* in their urine, none had gross evidence of pyelonephritis or renal stone formation and nearly all had normal kidneys histologically. The results are summarized in Table 3.

TABLE 3

| | | | | UNTREATED CONTROLS | | | | |
|---|---|---|---|---|---|---|---|---|
| Animal No. | Urine pH | Urine Vol. ml | Urine Acetohy. & mg/ml | Autopsy Urine bacteria/ml | Stone wt. mg | Stone Composition | Gross Kidney | Microscopic Kidney |
| 337 | Expired | | | | | | | |
| 338 | 8.6 | 8 | | $> 10^5$ | 25 | Struvite | Bilat. Papillary Stones | Pyelitis, Minimal Nephritis |
| 339 | 7.0 | 11 | | Sterile | 1 | Apatite | Normal | Normal |
| 340 | 8.1 | 17 | | $> 10^5$ | 40 | Struvite | Bilat. Papillary Stones & Bilat. Pyelonephritis | Pyelonephritis |
| 341 | 8.7 | 15 | | $> 10^5$ | 41 | Struvite | Bilat. Papillary Stones & Bilat. Pyelonephritis | Pyelonephritis with Papillary Necrosis |
| 342 | 8.7 | 7 | | $> 10^5$ | 84 | Struvite | Unilat. Pyelonephritis with no stones | Pyelonephritis with Papillary Necrosis |
| 343 | 8.6 | 11 | | $> 10^5$ | 56 | Struvite | Bilat. Pyelonephritis with Bilat. Papillary Stones | Pyelonephritis |
| 347 | 8.6 | 12 | | $> 10^5$ | 25 | Struvite | Unilat. Papillary Stones, Contralat. Pyelonephritis with Abscess | Pyelonephritis with Papillary Necrosis |
| 348 | Expired | | | | | | | |
| 349 | 8.5 | 13 | | $> 10^5$ | 94 | Struvite | Bilat. Pyelonephritis, Bilat. Papillary Stones | Pyelonephritis with Papillary Necrosis |

TABLE 3-continued

AHA TREATED

| Animal No. | Urine pH | Urine Vol. ml | Urine Acetohy. & mg/ml | Autopsy Urine bacteria/ml | Stone wt. mg | Stone Composition | Gross Kidney | Microscopic Kidney |
|---|---|---|---|---|---|---|---|---|
| 325 | 7.4 | 13 | .3 | > $10^5$ | 12 | Struvite | Normal | Pyelonephritis |
| 326 | 6.6 | 17 | 1.5 | > $10^5$ | 4 | Struvite | Normal | Mild Pyelitis, No Nephritis |
| 327 | 6.6 | 11 | 2.5 | > $10^5$ | 21 | Struvite | Normal | Normal |
| 328 | 6.7 | 12 | 1.3 | > $10^5$ | 4 | Struvite & Apatite | Normal | Normal |
| 329 | Expired | | | | | | | |
| 330 | 7.0 | 8 | .9 | > $10^5$ | 11 | Struvite | Normal | Normal |
| 331 | 6.3 | 17 | 1.5 | > $10^5$ | 1 | Apatite | Normal | Normal |
| 332 | 6.5 | 20 | 1.6 | > $10^5$ | 19 | Struvite | Normal | Normal |
| 333 | Expired | | | | | | | |
| 334 | 6.5 | 9 | 1.5 | > $10^5$ | 1 | Apatite | Normal | Mild Pyelitic No Nephritis |
| 335 | 6.3 | 16 | .5 | > $10^5$ | 3 | Struvite | Normal | Normal |
| 336 | 6.4 | 8 | 2.5 | > $10^5$ | 7 | Apatite | Normal | Normal | pH, urine volume, and acetohydroxamic acid concentrations are average of 3 day individual values. All autopsy urine specimen contained *Proteus mirabilis*, except animal No. 339.

It can be seen from the data in Table 3, that where the infected rats were given acetohydroxamic acid, while colonization of the urinary tract with bacteria continued the tissue damage and virulence of the disease decreased because acetohydroxamic acid maintained in urine pH in the physiological range. In addition it can be seen from the above data in Table 3 that the rats treated with the acetohydroxamic acid in accordance with the present invention had significantly less bladder stone formation than the control rats. This therefore establishes the ability of the acetohydroxamic acid not only to decrease stone formation and dissolve urinary tract stones but also to decrease or eliminate the pathogenicity of urinary colonization by urease producing bacteria.

While the present invention has been described primarily with regard to the foregoing exemplification, it should be understood that the present invention cannot under any circumstances be deemed as limited thereto but rather must be construed as broadly as any and all equivalents thereof.

What is claimed is:

1. A method of treating urinary infections which comprises administering to a patient suffering from a urinary infection associated with presence in the urine of bacteria of the species Proteus, an effective anti-bacterial dosage of a composition comprising in combination
   a. a dosage of methenamine which produces a concentration of methenamine in the patient's urine of from about 0.05 to about 1.0 mg/ml; and
   b. a dosage of acetohydroxamic acid which produces a concentration of hydroxamate groups in the patient's urine of from about 0.05 to about 2.0 mg/ml.

2. The method of claim 1, wherein said methenamine is administered in a dosage of about 0.5 to about 8.0 grams/day.

3. The method of claim 1, wherein said acetohydroxamic acid is administered in dosage of about 0.25 to about 4.0 grams/day.

4. A composition adapted to be administered to a patient suffering from a bacterial urinary infection comprising in combination:
   a. a dosage of methenamine which produces a concentration of methenamine in the patient's urine of from about 0.05 to about 1.0 mg/ml; and
   b. a dosage of acetohydroxamic acid which produces a concentration of hydroxamate groups in the patient's urine of from about 0.95 to about 2.0 mg/ml.

5. The composition of claim 4, wherein said methenamine is present in an amount to provide a dosage of about 0.5 to about 8.0 grams/day.

6. The composition of claim 4, wherein said acetohydroxamic acid is present in an amount to provide a dosage of about 0.25 to about 4.0 grams/day.

* * * * *

UNITED STATES PATENT OFFICE
CERTIFICATE OF CORRECTION

Patent No. 4024256            Dated May 17, 1977

Inventor(s) Donald P. Griffith, 4425 Hazelton; Daniel M. Musher, 4903 Heatherglen, both of Houston, Texas 77035

It is certified that error appears in the above-identified patent and that said Letters Patent are hereby corrected as shown below:

Column 6, Table 1-continued, structure is incorrect, should read

-- 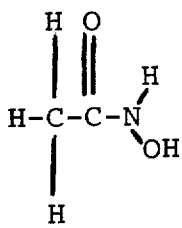 --;

In the claims:

Column 20 line 41, delete "0.95" and insert therefor -- 0.05 --.

Signed and Sealed this

Twenty-seventh Day of September 1977

[SEAL]

Attest:

RUTH C. MASON  
Attesting Officer

LUTRELLE F. PARKER  
Acting Commissioner of Patents and Trademarks